(12) United States Patent
Cheng

(10) Patent No.: US 6,359,687 B1
(45) Date of Patent: Mar. 19, 2002

(54) AEROSOL BEAM-FOCUS LASER-INDUCED PLASMA SPECTROMETER DEVICE

(75) Inventor: Meng-Dawn Cheng, Oak Ridge, TN (US)

(73) Assignee: Lockheed Martin Energy Research Corporation, Oak Ridge, TN (US)

(*) Notice: Subject to any disclaimer, the term of this patent is extended or adjusted under 35 U.S.C. 154(b) by 0 days.

(21) Appl. No.: 09/416,337

(22) Filed: Oct. 12, 1999

(51) Int. Cl.⁷ .............................................. G01N 21/63
(52) U.S. Cl. ...................................................... 356/318
(58) Field of Search .................................. 356/317, 318

(56) References Cited

PUBLICATIONS

Neuhauser et al., Laser–Induced Plasma Spectroscopy (LIPS): A Versatile Tool for Monitoring Heavy Metal Aerosols, Analytica Chimica Acta, vol. 392, Issue 1, Jun. 14, 1999, pp. 47–54.*

Publication by Marhavi Z. Martin, Meng–Dawn Cheng and Rodger C. Martin, entitled "Aerosol Measurement by Laser–Induced Plasma Technique: A Review," first submitted Aug., 1998, Aerosol Science and Technology, vol. 31, No. 6, Dec. 1999.

* cited by examiner

Primary Examiner—F. L. Evans
(74) Attorney, Agent, or Firm—Akerman Senterfitt

(57) ABSTRACT

An apparatus for detecting elements in an aerosol includes an aerosol beam focuser for concentrating aerosol into an aerosol beam; a laser for directing a laser beam into the aerosol beam to form a plasma; a detection device that detects a wavelength of a light emission caused by the formation of the plasma. The detection device can be a spectrometer having at least one grating and a gated intensified charge-coupled device. The apparatus may also include a processor that correlates the wavelength of the light emission caused by the formation of the plasma with an identity of an element that corresponds to the wavelength. Furthermore, the apparatus can also include an aerosol generator for forming an aerosol beam from bulk materials. A method for detecting elements in an aerosol is also disclosed.

25 Claims, 2 Drawing Sheets

Figure 1:
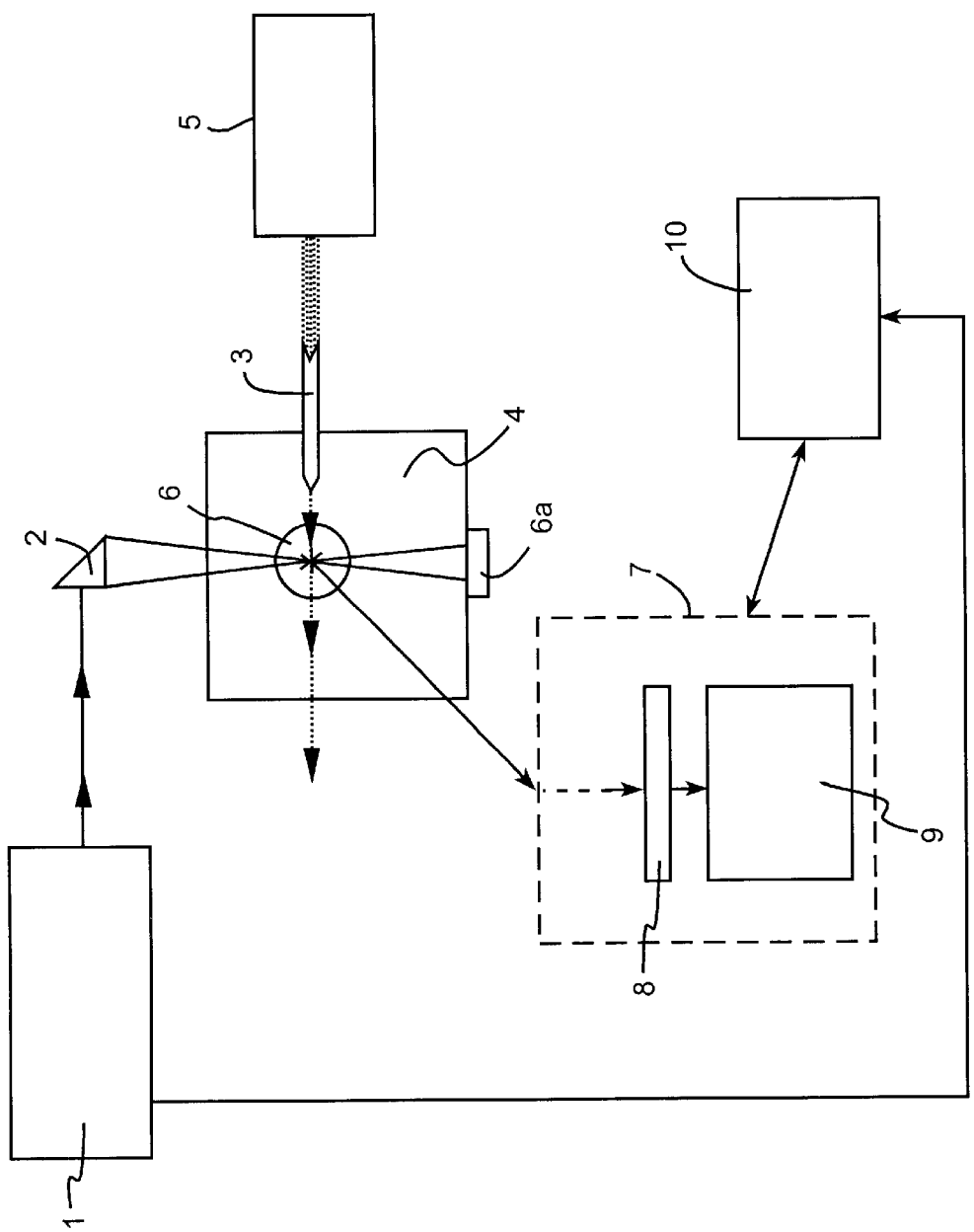

```
                  ┌──────────────┐
  ╭───────╮       │   PRODUCE    │
  │ START │ ────▶ │   AEROSOL    │
  ╰───────╯       └──────┬───────┘
                         ▼
                 ┌───────────────┐
                 │ CONCENTRATE THE│
                 │ AEROSOL INTO AN│
                 │  AEROSOL BEAM  │
                 └───────┬────────┘
                         ▼
                 ┌────────────────┐
                 │FOCUSING A LASER│
                 │INTO THE AEROSOL│
                 │BEAM IN ORDER TO│
                 │  FORM PLASMA   │
                 └───────┬────────┘
                         ▼
              ┌────────────────────────┐
              │ TRIGGER A DELAY TO     │
              │ DETECT AND MEASURE     │
              │ LIGHT EMISSIONS AT     │
              │ PREDETERMINED          │
              │ WAVELENGTHS CAUSED BY  │
              │ THE FORMATION OF PLASMA│
              └───────────┬────────────┘
                          ▼
                       ╱IS THE╲          ┌────────────────┐
                      ╱ DELAY  ╲   NO    │  WAIT FOR THE  │
                      ╲ PERIOD ╱ ──────▶ │ COMPLETION OF  │
                       ╲COMPL.╱          │ THE DELAY PERIOD│
                         │               └────────┬───────┘
                         │ YES                    │
                         ▼                        │
              ┌──────────────────────┐            │
              │ DETECT LIGHT         │◀───────────┘
              │ EMISSIONS CAUSED BY  │
              │ THE FORMATION OF     │
              │ PLASMA AND MEASURE   │
              │ THE INTENSITY OF     │
              │ THESE LIGHT EMISSIONS│
              └──────────┬───────────┘
                         ▼
              ┌──────────────────────┐
              │ CORRELATE THE        │
              │ DETECTED LIGHT       │
              │ EMISSIONS WITH THE   │
              │ CORRESPONDING        │
              │ ELEMENTS FOUND IN    │
              │ THE AEROSOL          │
              └──────────┬───────────┘
                         ▼
              ┌──────────────────────┐
              │ CORRELATE THE        │      ╭───────╮
              │ INTENSITY OF THE     │ ────▶│  END  │
              │ MEASURED LIGHT       │      ╰───────╯
              │ EMISSIONS WITH THE   │
              │ AMOUNT OF ELEMENTS   │
              │ FOUND IN THE AEROSOL │
              └──────────────────────┘
```

*FIG. 2*

AEROSOL BEAM-FOCUS LASER-INDUCED PLASMA SPECTROMETER DEVICE

STATEMENT REGARDING FEDERALLY SPONSORED RESEARCH

This invention was made with United States Government support awarded by the Department of Energy to Lockheed Martin Energy Research Corporation, Contract No. DE-AC05-96OR22464. The United States Government has certain rights in this invention.

CROSS-REFERENCE TO RELATED APPLICATIONS (Not Applicable)

BACKGROUND OF THE INVENTION

1. Field of the Invention

This invention relates to the measurement of particulate matter. More specifically, this invention relates to the in-situ, real-time measurement of elements associated with aerosols.

2. Description of the Relevant Art

Several metals, such as mercury, arsenic, and chromium, among others, are toxic to human health and to certain ecosystems. The United States Environmental Protection Agency has planned to regulate the emission of these, as well as other, metals. Proper determination of compliance with these potential regulations requires measurement of metal emissions to be made. Traditional means for detecting or measuring these and other emissions are time-consuming, labor intensive, and extremely costly. Traditional detecting or measuring means used filter-based time-integrated sampling schemes followed by laboratory analysis by trained laboratory technicians. These measurements typically take a period of several hours to perform, and offer little use to continuous emission monitoring, pollution control, and/or particle toxicological research that requires a large number of data measurements to be made on a high volume of emissions very often. Additionally, a variety of sampling artifacts could exist that complicate collection of representative data. For instance, in-situ nucleation and coagulation can alter particle size distribution and chemical composition as a function of particle sizes, leading to inaccurate data when dilution sampling is employed. Solving such a complication is difficult, and no general solution is available. These schemes are also problematic in that they are not particularly good for use in hazardous environments, such as those that are hot, radioactive, and/or oxygen deficient. This forecloses the adequate measurement of elements in environments in which the monitoring of particulate matter is particularly important.

Real-time, in-situ measurement is the best and probably the only solution for detecting or measuring particulate matter in a hazardous environment. Real time physical and chemical classification of particulate matter can provide direct measurements of the dynamics and phase partition, as well as the transformation of aerosols and chemical species associated with aerosol particles. However, there is currently no commercially available instrument for the continuous measurement of emissions in a hazardous environment, among others.

A compact laser-based instrument was developed for detecting or measuring elements found in aerosol particles. This instrument made measurements of these elements using laser-induced plasma spectroscopy (LIPS). LIPS is an established technique for detection of metals in various matrices such as solid, liquid, gas, and/or aerosol particulate matter. LIPS requires no alteration of the condition of a sample, because the measurement of samples is performed in situ. Furthermore, LIPS has a response time on the order of seconds, which is extremely short and which allows the LIPS system to perform measurements in real time. Applications of LIPS systems have been limited, however, due to their lack of sensitivity as compared to other atomic emission spectrometric techniques, such as inductively coupled plasma/atomic emission spectroscopy (ICP/AES), among others.

The LIPS technique has several advantages over the other traditional analytical techniques for particle measurement. These advantages include rapid turn-around time, non-invasive, in-situ, flexible configuration, and the readiness of a LIPS device for use in building a compact trace metal analyzer. These strengths make LIPS an attractive candidate for the development of a field-portable, multi-element monitor for use in a hazardous environment such as a radiological hot cell, a mix-waste contaminated area, or a high-temperature combustion chamber. A LIPS with a high degree of sensitivity may also be a good instrument for performing environmental and/or health research. Unfortunately, a LIPS for these uses is not commercially available at the current time.

A problem with the LIPS technique is that it cannot, on its own, detect metals, such as mercury or chromium, among others, in aerosols at a level commonly found in source emissions. The LIPS technique, on its own, has never before detected mercury or chromium in a field test. To raise the instrument's analytical performance, a number of proposals were tested. In Sattman, R. et al. (1995) *J. Phys. D.:Appl. Phys.*, 28, 2181–2187, the use of double or multiple laser pulses to achieve higher signal-to-noise ratios for detecting Si in solid steel samples was demonstrated. It was found that double pulses enhanced the signal over single pulses used in traditional LIPS by 2 orders of magnitude. In Gornushkin et al. (1997), Appl. Spectrosc., 51(7):1055–59, the use of a LIPS/Laser-excited atomic fluorescence spectrometry technique for the determination of cobalt in solid sample matrices, such as graphite, soil, and steel, was suggested. They found the combination offered a technique that has linearity over four orders of magnitude in the ppb to ppm range, and the analytical result was comparable to ICP/AES. However, while these sensitive techniques provide greater detection levels for metals and appear to yield better analytical results than a single-pulse LIPS, they still do not provide a way to make a LIPS-based device that can be miniaturized, user friendly, and field portable. Additionally, these techniques have not been demonstrated to be applicable to aerosol measurement.

BRIEF SUMMARY OF THE INVENTION

It is an object of the invention to provide a method and apparatus for the continuous in situ detection or measurement of elements associated with particulate matter.

It is another object of the invention to provide a method and apparatus for the real-time detection or measurement of elements associated with particulate matter.

It is still another object of the invention to provide an apparatus for the detection or measurement of elements associated with particulate matter that is reduced in size and preferably portable.

Another object of the invention is to provide a method and apparatus for detecting or measuring elements associated with particulate matter that has acceptable precision.

These and other objects of the invention are achieved by the subject apparatus for detecting elements in a given environment, which comprises an aerosol beam focuser for concentrating an aerosol into an aerosol beam and a laser and a detection device for detecting the elements found in the aerosol beam and measuring the quantities of these elements. The laser induces the initiation and formation of plasma from the aerosol beam. The detection device may comprise, among other things, a spectrometer for detecting spectral emissions of the aerosol particles caused by the initiation and formation of the aerosol particles into plasma. The apparatus may further comprise a processor for correlating the spectral emissions caused by the formation of plasma with the elements and the amounts of the elements corresponding to these spectral emissions. This apparatus may also comprise an aerosol generator for producing aerosol particles from bulk particulate matter.

In the present invention, the aerosol beam focuser is preferably a nozzle. In the present invention, the detection device is preferably a laser-induced plasma (or breakdown) spectrometer (LIPS). The laser used in the LIPS is preferably a high-energy laser beam. Furthermore, the beam of the laser used in the LIPS preferably has a short pulse. The spectrometer used in the LIPS is preferably a combination of at least one grating and an intensified charge-coupled device.

An additional embodiment of the invention is a method for detecting elements in a given environment, which comprises concentrating an aerosol into an aerosol beam, and detecting the elements and measuring the amounts of the elements in the aerosol, among other things. The step of detecting the elements and measuring the amounts of the elements in the aerosol can also further comprise the steps of forming plasma from the aerosol, and detecting spectral emissions caused by the formation of plasma to determine the identity of the elements contained in the aerosol. The step of detecting the elements and measuring the amounts of the elements in the aerosol beam can further comprise the step of measuring the intensity of the spectral emissions caused by the formation of plasma to determine the amount of the elements contained in the aerosol beam.

There is no specific restriction as to the manner in which plasma can be formed from the aerosol particles. In the present invention, the aerosol particles are preferably transformed into plasma through the use of a laser. The laser preferably has a short pulse and emits a high-energy beam. Furthermore, the aerosol particles are concentrated and the laser beam is preferably fired and focused through an optical lens array, among other things, so that the aerosol particles and the laser beam intersect one another. Such an intersection allows the use of a comparatively lower energy laser for transforming the concentrated aerosol particles found in the aerosol beam into plasma, than had the aerosol particles not been concentrated.

There is no specific restriction as to the manner in which the identity and amount of the elements contained in the plasma can be measured. When the laser transforms the aerosol beam into plasma, light is emitted which can be detected and measured to determine the identity and amount of the elements present in the plasma. Consequently, the identity and amount of the elements present in an aerosol beam can be determined. In the present invention, such detection and measurement is preferably made using spectroscopy.

BRIEF DESCRIPTION OF THE DRAWINGS

FIG. 1 illustrates an apparatus for detecting elements in a given environment according to the present invention.

FIG. 2 illustrates a method for detecting elements in a given environment according to the present invention.

DETAILED DESCRIPTION OF THE INVENTION

Referring to FIG. 1, an apparatus for detecting elements in a given environment, according to the present invention, is illustrated. The apparatus comprises a laser 1 that emits a laser beam; an optical lens array 2 that focuses the laser beam emitted by the laser 1; an aerosol beam focuser 3 that concentrates aerosol into an aerosol beam; a chamber 4 into which the laser 1 that has been focused by the optical lens array 2 is fired and into which the aerosol beam focuser 3 emits the aerosol beam; and a detection device 7 for detecting light emissions given off by a reaction between the laser pulse emitted by the laser 1 and the beam of concentrated aerosol particles emitted by the aerosol beam focuser 3, as well as for measuring the intensity of these emissions, among other things. The apparatus may also comprise a processor 10 for correlating the light emissions and the intensity of the light emissions detected by the detection device 7 to elements associated with these light emissions and the amounts of these elements.

There is no specific restriction as to the type of laser 1 that may be used in the present invention. The laser 1 should generally be a solid state laser, because it is preferable that the laser be reduced in size and portable. Any other laser, such as a gas laser, will also be preferable for use in the present invention if it can be made in a manner that allows the reduced size and portability preferences of the present invention to be fulfilled. The laser 1 should also generally fire a pulsed laser beam, because the laser should generally fire a beam with a high enough power to cause the formation of plasma from aerosol particles and lasers that fire a pulsed laser beam are generally the only lasers with sufficiently high power at the present time. If, however, a continuous wave laser, or any other type of laser, is produced in a manner that allows the laser to fire a beam with a high enough power to cause the formation of plasma from aerosol particles, that laser would be sufficient for use in the present invention. The power of the beam, or pulse, fired by the laser 1 can be monitored using the photodetector 6 and the optical power meter **6*a*** to ensure that a high enough power beam is being fired at any given time.

The optical lens array 2 is necessary if the laser beam fired by laser 1 cannot cause plasma formation in an unfocused state. The optical lens array 2 can be any device which can focus the laser beam of the laser 1 sufficient to induce the formation of plasma from aerosol particles. In general, the optical lens array may be one or more lenses, among other things. The size of the lens used will depend on the size of the laser 1 used, the diameter of the laser beam fired by the laser 1, and the desired diameter of the pulse in order to induce plasma formation.

The aerosol beam focuser 3 can be any device that concentrates an aerosol into an aerosol beam. The aerosol beam focuser 3 generally allows a lower power and smaller size laser to be used in the present invention. The aerosol beam focuser 3 should preferably have the ability to constantly concentrate the aerosol into the aerosol beam. For example, such concentrating can generally be achieved through the use of a mechanism with a larger input diameter than output diameter, such as a nozzle. In the present invention, the aerosol beam focuser 3 is preferably a nozzle. The nozzle should generally produce an aerosol beam with a diameter lesser than or equivalent to the diameter of the laser beam fired by the laser 1 at the aerosol beam. Producing an aerosol beam with this diameter allows substantially the entirety of the aerosol beam to be formed into plasma when it reacts with the laser beam fired by the laser 1. The aerosol beam focuser 3 can be produced using any material. For example, the aerosol beam focuser 3 can be constructed from stainless steel, brass or aluminum, among other materials. However, it is preferable that the aerosol beam focuser 3 be produced from a material that requires reduced cleaning and maintenance, and that has a high degree of chemical resistivity. Thus, in the present invention, it is preferable that the aerosol beam focuser 3 be constructed of stainless steel.

The pulse emitted by the laser 1 and subsequently focused by the optical lens array 2 reacts with the aerosol beam formulated by the aerosol beam focuser 3 in the chamber 4. The laser beam and the aerosol beam preferably intersect in the chamber 4 so that each pulse of the laser beam forms plasma from the aerosol beam. The chamber 4 is preferably reduced in size, as it is preferred that the present invention be portable. The chamber 4 should generally be hollow to some degree and have at least five openings which allow: 1) the laser pulse to enter the chamber 4; 2) the laser pulse to exit the chamber 4; 3) the aerosol beam to enter the chamber 4; 4) the aerosol beam to exit the chamber 4; and 5) light emitted from the formation of plasma to exit the chamber 4.

The chamber 4 should be constructed of a material that can withstand the light emissions caused by the reaction between the laser beam fired by the laser 1 and the aerosol beam produced by the aerosol beam focuser 3, such as stainless steel, brass or aluminum, among other materials. Furthermore, like the aerosol beam focuser 3, the chamber 4 should be constructed of a material that requires reduced cleaning and maintenance, and that has a high degree of chemical resistivity. In the present invention, the chamber 4 is preferably constructed of stainless steel.

The focusing of the laser beam inside the chamber 4 produces energy flux density conditions inside the focal volume of the laser 1 that will cause all material inside the plasma to vaporize. The focal volume of the laser 1 is the volume of the laser beam at the focal point produced by focusing this laser beam with the optical lens array 2. These energy flux density conditions rely on both the laser 1 and the optical lens array 2 used in the present invention. The vaporizing of the material inside the plasma causes all atoms within this aerosol beam to be elevated to excited states almost instantly. For example, in the present inventions the electric flux density conditions within the focal volume of the laser 1 can potentially reach a level on the order of around 25 GW/cm$^2$, which can create plasma with a core temperature reaching 25,000K or higher. Depending on the laser 1 and optical lens array 2 used in the present invention, and the electric flux density produced thereby, the plasma created can reach any number of temperatures. All of the material inside this plasma volume is vaporized. As a result of the violent energy-matter interactions occurring in the plasma from the vaporization of the material inside, millions and billions of energetic ions and electrons are produced. After the laser pulse is completed, the excited atoms will generally begin to relax to their approximate ground states. When this occurs, these atoms will emit broadband light at specific wavelengths.

The broadband light that is emitted from the relaxation of the ions and electrons from their plasma-excited states is detected or measured using the detection device 7. The detection device 7 can be any device that can identify elements found in the aerosol beam produced by the aerosol beam focuser 3. The detection device 7 can also preferably make measurements of the amount of identified elements that are present in the aerosol beam. The detection device 7 is preferred to have reduced size and to be portable.

In the present invention, the preferred detection device 7 is a spectrometer, among other things. Any type of spectrometer that can detect and measure the light emitted from the formation of plasma from the aerosol beam can be used in the present invention. For example, the spectrometer can be either a grating and intensified charge-coupled device or a diode array, among other things. However, in the present invention it is preferred that the spectrometer comprise at least one grating 8 and an intensified charge-coupled detector (ICCD) 9. Furthermore, it is preferable that the ICCD be gated.

The detection device 7 collects the broadband light released by the relaxation of the excited atoms to their ground states and separates the broadband light by wavelength. This collection and separation can generally be accomplished using the at least one grating 8, among other things. Multiple gratings may be necessary depending on the range of wavelengths that are desired to be monitored using the present invention. For example, if the present invention is desired to be used to monitor wavelengths between approximately 200 nm and 500 nm, then one grating could be used in the detection device 7. However, if the present invention is desired to be used to monitor wavelengths between approximately 200 nm and 900 nm, then two, or possibly three, gratings 8 would be necessary to separate all of the wavelengths found in that desired spectrum. As such, different gratings 8 may be used in place of those used in the preferred embodiment of the present invention if the wavelengths of the materials that are desired to be measured by the present invention are greater or lesser in size or volume than those measured in the preferred embodiment.

The broadband light that is collected and separated by the at least one grating 8 is then transmitted to the ICCD 9, which detects the wavelengths of the broadband light separated by the at least one grating 8 and measures the intensity of the wavelengths. There is no specific restriction as to the construction of the ICCD 9 in the present invention. The ICCD 9 merely needs to be able to detect the wavelengths of the broadband light emissions induced by the formation of plasma in the chamber 4 for any elements that are desired to be detected by the present invention. Also, the ICCD need preferably be able to measure the intensity of the wavelengths of the broadband light emissions induced by the formation of plasma in the chamber 4 to determine the amounts of any elements that are desired to be measured by the present invention. Furthermore, the ICCD 9 need preferably have the ability to detect or measure wavelengths for multiple elements over a short period of time. Thus, the ICCD 9 may be gated so that detection or measurements of wavelengths separated by the at least one grating 8 are made at different time intervals rather than continuously.

When the laser 1 fires the laser beam, a trigger signal may be sent by the laser 1 to the processor 10 that causes the processor 10 to delay detection or measurement of emitted light by the detection device 7, such as the spectrometer including the at least one grating 8 and ICCD 9, among other things, for a pre-programmed time interval. This delay is not required by the present invention, as the detection device 7 can continuously detect or measure broadband light emitted by the formation of plasma from the aerosol beam. However, if the delay trigger is used, the time interval of the delay of measurement of emitted broadband light by the detection device 7 is approximately equivalent to the time that it takes each element that is sought to be detected or measured to reach a relaxed state and emit light during the formation of plasma from the aerosol beam.

The delay time between the laser 1 firing and the detection by the ICCD 9 is usually around a few to ten microseconds, depending upon the elements that are desired to be measured and the configuration of the detection device 7 being used. This delay time needs to be obtained experimentally by determining the amount of time that it takes each element to return to a relaxed state during the formation of plasma. For example, in the present invention the delay time for mercury and chromium was found to be optimal at about 7 to 17 microseconds, respectively. Thus, when the detection or measurement of mercury is desired, the processor 10 will delay the detection and measurement of the intensity of light emitted by the detection device 7 for about seven microseconds. When the detection or measurement of chromium is desired, the processor 10 will delay the measurement by the detection device 7 for about seventeen microseconds. The detection device 7 will then generally look to detect or measure the intensity of light emitted for a period of about 2 to 10 microseconds, depending on the species of element that is desired to be detected or measured. When more than one element is sought to be determined in a material, the processor 10 will generally instruct the laser and detection device 7 to repeat these processes.

All of the processes of the laser 1 and detection device 7 preferred in the present invention, such as the breakdown of aerosol particles into plasma, ignition of this plasma, triggering the emission of light from the formation of plasma, collection and separation of the output light, performing a spectral analysis on the separated light wavelengths, and data processing to determine the identity and amount of the elements associated with the output light wavelengths, among others, preferably occur during the pulse period of the laser 1. This pulse period of the laser 1 is measured from the start of one laser beam being fired to the start of the next laser beam being fired.

For example, in the present invention, the preferred laser 1 fires laser beams at a pulse rate of 10 Hz. Thus, the processes of the laser 1 and detection device 7, which combination forms a laser-induced plasma spectrometer, used in the present invention are preferably completed in a period of approximately 100 milliseconds. With this data-throughput rate of 100 milliseconds, the laser-induced plasma spectrometer preferred in the present invention can function as a real-time monitoring system, such as a continuous metal emission monitor, among other things, as long as this preferred embodiment of the present invention can maintain its performance at extreme source conditions for a sustained period. If a laser 1 with a different pulse period is used, or if the pulse period is changed in the preferred laser 1, the period of time in which the processes of the present invention are preferably completed will change.

By carefully determining the wavelength or wavelengths of light corresponding to an element or elements, respectively, identification of the element or elements can generally be made through the use of the processor 10. This is accomplished by the ICCD 9 sending to the processor 10 the measurements of the light wavelengths emitted from the formation of plasma from the aerosol beam and the corresponding intensity of these wavelengths, and the processor 10 then correlates these measurements with known light wavelengths associated with given elements. The processor 10 can also generally use the light intensity of the wavelength or wavelengths measured by the at least one grating 8 and the ICCD 9 to make a quantitative determination of the amount or concentration of the measured elements present in the aerosol beam, as well.

In the embodiment of the invention illustrated in FIG. 1, the laser 1 is preferably a Q-switched Nd:YAG laser that fires a pulse having a wavelength of about 532-nm and a repetition rate of approximately 10 Hz. This laser 1 preferably has a minimum energy of about 20–30 mJ per pulse, and generally generates a pulse having an energy measurement of about 100 mJ per pulse. The optical lens array 2 is a single lens able to focus the pulse of the laser 1 so that the energy flux density inside the focal volume of the laser 1 reaches at least around 2 $GW/cm^2$, and generally about 25 $GW/cm^2$. The aerosol beam focuser 3 is a nozzle having geometry of 20 degrees of the converging angle of the nozzle over a 2 mm linear length, or 40 degrees, and an exit diameter of about 0.32 cm. Furthermore, the aerosol beam passed through this nozzle preferably has a flow of approximately 5 l/min at around 1 atmosphere of pressure. The chamber 4 is preferably a cube having windows on five of its six sides, and having sides measuring about two inches. Furthermore, the chamber 4 is constructed of stainless steel. The detection device 7 is a spectrometer including three gratings 8 and an ICCD 9. Two of these gratings 8 have a concentration of approximately 1200 grooves/mm and the third grating 8 has a concentration of approximately 150 grooves/mm. The ICCD 9 has a linear configuration of about 1024×256 pixels and a minimal gate of approximately 1.2 nanoseconds. Furthermore, the ICCD 9 has about 26 micrometer size pixels for photon counting. The processor 10 in this example is a laptop computer.

The laser 1 used in the present may also possibly be configured to use fiber optic delivery, among other things, such that the present invention can be used in an environment that requires a flexible energy delivery probe, such as in the mining industry, among other environments. The laser 1 may also be reduced in size so that it uses, among other things, a diode-pump passively Q-switched laser.

If the present invention as illustrated in FIG. 1 is desired to be used for measuring bulk materials, then an aerosol generator 5 must be used to transform the bulk materials into an aerosol. The aerosol generator 5 is not restricted to any specific device for forming the aerosol, it can be any of a number of common commercial products, such as an atomizer, among other things. The aerosol generator 5 should be able to convert bulk materials into the aerosol, such as air potentially containing metals, chemicals or other hazardous materials, among other things. In the present invention, the aerosol generator 5 should be able to produce monodisperse and polydisperse particles or a gas permeation source for producing a known gas concentration.

For example, one possible aerosol generator 5 could include a 3-jet hypersonic head and a jet atomizer, among other things. This aerosol generator 5 includes a 3-jet hypersonic head and a jet atomizer, and preferably is capable of producing particles with a number median diameter of around 0.3 micro-meters and a geometric standard deviation of 1.9, and with a number density on the order of around $10^5$ to $10^7$ per cc of gas, which is approximately the number density of particles that is found in industrial stacks. Another possible aerosol generator 5 could be used to produce an aerosol from a metal, with metal-embedded uniform particles in the aerosol potentially having a size in between around 100 and 500,000 nm, among other things. The aerosol generator 5 may produce an aerosol from bulk materials in any of a number of ways. The size of the particles in the aerosol produced can be measured and the aerosol generator 5 can be made to produce these particles within a given size or concentration range. However, no specific particle size or number concentration (or density) of aerosol particles (or gas particles) is required for materials in the aerosol (or gas) to be measured by the present invention.

Referring to FIG. 2, a method for detecting elements in a given environment, according to the present invention, is illustrated. This method comprises the steps of concentrating an aerosol into an aerosol beam, firing a laser into the aerosol beam to form plasma, and detecting light emissions caused by the plasma formation. This method may also comprise the step of measuring the intensity of the light emissions caused by the plasma formation. This method may further comprise the step of correlating the detected or measured light emissions with the elements or the amounts of the elements, respectively, to which the light emissions correspond.

The step of concentrating the aerosol into an aerosol beam can be accomplished in any manner. The aerosol beam need only be concentrated in such a manner as to allow the transfer of an increased number of aerosol particles to the focal volume of the laser being fired into the aerosol beam. The transfer of an increased number of aerosol particles to the focal volume of the laser is achieved by concentrating the aerosol into an aerosol beam with a diameter lesser than or equivalent to the diameter of the laser being fired into the aerosol beam. By concentrating the aerosol beam, a higher degree of uniformity of particles can be found across the aerosol beam, causing an increased number of aerosol particles to be transferred to the focal volume of the laser and formed into plasma. This concentrating increases the efficiency of the reaction between the aerosol beam and the laser, and results in an increased production of plasma and, consequently, a greater degree of light emissions for measurement.

There are no specific restrictions as to the manner in which the laser should be fired, except that the firing of the laser should cause the aerosol beam to form plasma. The laser may have to be focused when it is fired in order to cause the formation of plasma from the aerosol beam. Generally, plasma formation is accomplished when the laser is fired in any manner that allows the laser beam to intersect with the aerosol beam with enough energy to induce the formation of plasma from the aerosol beam. Firing the laser so that it intersects with the aerosol beam allows each laser pulse to form plasma from the portion of the aerosol beam with which it intersects. The laser beam is not required to be continuous; a laser pulse can be fired at the aerosol beam. However, it is generally preferred that if the laser beam is a laser pulse, then the pulse be short in duration so the signal-to-noise ratio can be enhanced.

In the present embodiment of the invention, any detection or measurement methodology can be used as long as the identity of an element that was in the aerosol beam, and that was subsequently transformed into plasma, can be determined. For example, in the present embodiment of the invention, detection of the wavelength of light emitted by the formation of plasma from the element that was in the aerosol beam can be used to determine the identity of that element. Furthermore, it is preferred that a measurements of the amount of the element that was present in the aerosol beam can also be determined by the light emitted by the formation of plasma from the element that was in the aerosol beam. For example, in the present embodiment of the invention, measurement of the intensity of the light emitted by the formation of plasma from the element that was in the aerosol beam can be used to determine the amount of the element that was present in the aerosol beam. In the present embodiment of the invention, these detections or measurements can be made using spectroscopy, among other things.

The firing of the laser may be used to trigger a delay of the detection or measurement of the wavelengths of the light emissions. This delay potentially allows for the detection or measurement of the wavelengths of specific elements at the time in the plasma formation cycle during which these elements emit light, rather than the continuous measurement all elements. While continuous detection is still one possible method for detecting the wavelengths of the elements sought to be identified, this detection methodology may be less efficient. If two elements emit the same light wavelength during formation of plasma, then this delay might also provide a method for distinguishing these two elements from one another.

There is no specific restriction as to the manner in which the detected light emissions can be correlated with their corresponding elements. Furthermore, there is also no specific restriction as to the manner in which the measurement of the intensity of the light emissions can be correlated with the corresponding amounts of the elements. Any manner that is currently known in the art, or that is known in the art in the future, may be sufficient to correlate detected light emissions and the measured intensity of the light emissions to their corresponding elements and the amounts of these elements, respectively. These correlations need only allow elements and their amounts to be determined from the results of the detection or measurement methodology used in the present invention. In the present embodiment of the invention, which detects the light emitted from the formation of plasma from the elements in the aerosol beam and measures the intensity of the light emissions, the correlation is performed by matching the wavelength of the detected light emissions and its measured intensity to the corresponding known wavelength of these elements. When a match between measured wavelengths and known wavelengths is found, then the element is identified as that having the matching known wavelength and the amount of the element is determined from the intensity of the light emission to which it corresponds.

In the present embodiment of the invention, the amount of the element present in the aerosol beam is determined by the intensity of the light emitted. For example, the more intense the measured light emission, the greater the amount of the element present in the aerosol beam. The exact amount of the elemental concentration would have to be determined from a calibration curve.

If bulk solid or liquid materials are desired to be detected or measured using the present method for detecting measuring elements in a given environment, the method may further comprise the step of transforming the bulk materials into an aerosol prior to concentrating the aerosol into an aerosol beam. This formation of an aerosol from bulk materials allows the present invention to be used to measure elements that are in non-aerosol substances, such as solids or liquids, among other things. This transformation can be done using any method provided that the aerosol produced is able to be concentrated and focused into plasma, among other things. The present invention may be used for many different forms of material measurements, including those used in process monitoring and environment and/or health compliance, among other things.

It should be understood that the examples and embodiments described herein are for illustrative purposes only and that various modifications or changes in light thereof will be suggested to persons skilled in the art and are to be included within the spirit and purview of this application.

The invention can take other specific forms without departing from the spirit or essential attributes thereof, and reference should be had to the following claims rather than this specification in order to determine the scope of the invention.

What is claimed is:

1. An apparatus for detecting elements in an aerosol, comprising:

an aerosol beam focuser for concentrating aerosol into an aerosol beam;

a laser for directing a laser beam into the aerosol beam to form a plasma; and a detection device that detects a wavelength of a light emission from at least one element caused by the formation of the plasma.

2. An apparatus for detecting elements in an aerosol according to claim 1, further comprising a processor that correlates the wavelength of the light emission of the at least one element caused by the formation of the plasma with an identity of the at least one element that corresponds to the wavelength.

3. An apparatus for detecting elements in an aerosol according to claim 1, wherein the aerosol beam has a smaller cross-sectional area than the laser beam.

4. An apparatus for detecting elements in an aerosol according to claim 2, further comprising an aerosol generator for forming an aerosol beam from a bulk material.

5. An apparatus for detecting elements in an aerosol according to claim 2, wherein the aerosol beam focuser is a nozzle.

6. An apparatus for detecting elements in an aerosol according to claim 5, wherein the nozzle is constructed of stainless steel.

7. An apparatus for detecting elements in an aerosol according to claim 2, wherein the laser is a solid state laser.

8. An apparatus for detecting elements in an aerosol according to claim 7, wherein the laser is a Nd:YAG laser.

9. An apparatus for detecting elements in an aerosol according to claim 8, wherein the laser fires a pulse rather than a continuous wave.

10. An apparatus for detecting elements in an aerosol according to claim 9, wherein any pulse fired by the laser has an minimum energy value of 20 mJ.

11. An apparatus for detecting elements in an aerosol according to claim 2, wherein the detection device also measures an intensity of the wavelength of the light emission from the at least one element caused by the formation of the plasma.

12. An apparatus for detecting elements in an aerosol according to claim 2, wherein the processor also correlates the intensity of the wavelength of the light emission of the at least one element caused by the formation of the plasma with an amount of the at least one element that corresponds to the wavelength.

13. An apparatus for detecting elements in an aerosol according to claim 2, wherein the detection device is a spectrometer.

14. An apparatus for measuring elements in an aerosol according to claim 13, wherein the spectrometer further comprises:

at least one grating for separating broadband light; and an intensified charge-coupled device for measuring the separated broadband light.

15. An apparatus for measuring elements in an aerosol according to claim 2, wherein the processor is a computer.

16. A method for detecting elements in an aerosol, comprising the steps of:

concentrating aerosol into an aerosol beam;

directing a laser beam at the aerosol beam to form plasma;

detecting at least one wavelength of a light emitted by the plasma formed by said directing of the laser beam at the aerosol beam.

17. A method for detecting elements in an aerosol according to claim 16, further comprising the step of correlating the at least one wavelength of the light emitted by the plasma formed by said directing of the laser beam at the aerosol beam to an element that corresponds to each of the at least one wavelengths.

18. A method for detecting elements in an aerosol according to claim 17, further comprising the step of forming an aerosol beam from a bulk material.

19. A method for detecting elements in an aerosol according to claim 17, wherein the step of directing a laser beam at the aerosol beam to form plasma is accomplished by focusing the laser beam through an optical lens array.

20. A method for detecting elements in an aerosol according to claim 19, wherein the laser beam that is focused has a cross-sectional area that is larger than or equivalent to the aerosol beam.

21. A method for detecting elements in an aerosol according to claim 17, wherein the step of concentrating an aerosol beam into an aerosol beam is accomplished through the use of an aerosol beam focuser.

22. A method for detecting elements in an aerosol according to claim 17, wherein the step of detecting at least one wavelength of a light emitted by the plasma formed by said directing of the laser beam at the aerosol beam is accomplished by separating each of the at least one wavelengths from the light emitted by the plasma and detecting each of the at least one wavelengths separated from the light emitted by the plasma.

23. A method for detecting elements in an aerosol according to claim 17, further comprising the steps of:

measuring an intensity of the at least one wavelength of the light emitted by the plasma formed by said directing of the laser beam at the aerosol beam; and correlating the intensity of the at least one wavelength of the light emitted by the plasma formed by said directing of the laser beam at the aerosol beam to an amount of the element that corresponds to each of the at least one wavelengths.

24. A method for detecting elements in an aerosol according to claim 23, wherein the step of measuring the intensity of the at least one wavelength of the light emitted by the plasma formed by said directing of the laser beam at the aerosol beam is accomplished by separating each of the at least one wavelength of the light emitted by the plasma formed by said directing of the laser beam at the aerosol beam, and measuring the intensity of each of the separated at least one wavelengths.

25. A method for detecting elements in an aerosol according to claim 23, wherein the step of correlating the intensity of the at least one wavelength of the light emitted by the plasma formed by said directing of the laser beam at the aerosol beam to an amount of the element that corresponds to each of the at least one wavelengths is accomplished through the use of a computer.

* * * * *